United States Patent [19]

Skiles et al.

[11] Patent Number: 4,496,542
[45] Date of Patent: Jan. 29, 1985

[54] N-SUBSTITUTED-AMIDO-AMINO ACIDS

[75] Inventors: Jerry W. Skiles, Tuckahoe; Raymond D. Youssefyeh, Tarrytown, both of N.Y.; John T. Suh, Greenwich, Conn.; Howard Jones, Ossining, N.Y.

[73] Assignee: USV Pharmaceutical Corporation, Tarrytown, N.Y.

[21] Appl. No.: 484,729

[22] Filed: Apr. 13, 1983

Related U.S. Application Data

[63] Continuation-in-part of Ser. No. 249,053, Mar. 30, 1981, abandoned.

[51] Int. Cl.³ ............... A61K 37/00; A61K 31/40; A61K 31/425; C07C 103/52; C07D 403/00; C07D 233/66; C07D 233/28; C07D 233/00; C07D 235/04; C07D 405/00; C07D 211/72; C07D 211/56; C07D 211/30; C07D 215/00; C07D 221/02; C07D 415/00; C07D 413/00; C07D 265/30; C07D 279/10

[52] U.S. Cl. ........................ 514/2; 424/271; 260/112.5 R; 548/517; 548/527; 548/567; 548/146; 548/518; 548/557; 548/336; 548/337; 548/348; 548/351; 548/300; 548/325; 548/195; 548/490; 548/469; 546/277; 546/309; 546/209; 546/244; 546/247; 546/164; 546/112; 544/133; 544/141; 544/164; 544/58.1; 544/58.5; 544/58.7; 549/467; 549/57

[58] Field of Search ................ C07D/401/00; 260/112.5 R; 424/177, 274, 270, 271; 548/517, 518, 348, 527, 557, 351, 567, 336, 300, 146, 337, 325, 195, 490, 469; 546/277, 309, 209, 244, 247, 164, 112; 544/133, 141, 164, 58.1, 58.5, 58.7; 549/467, 57, 480, 493, 69

[56] References Cited

FOREIGN PATENT DOCUMENTS 50800 5/1982 European Pat. Off. ..... 260/112.5 R

*Primary Examiner*—Delbert R. Phillips

[57] ABSTRACT

Compounds of the formula

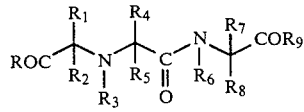

wherein
R and $R_9$ are independently hydroxy and lower alkoxy,
$R_1$ and $R_2$ are independently hydrogen, lower alkyl, aryl-lower alkyl having from 7 to 12 carbon atoms, or heterocyclic-lower alkyl having from 6 to 12 carbon atoms,
$R_3$, $R_4$, $R_5$, $R_7$ and $R_8$ are hydrogen or lower alkyl,
$R_6$ is heterocyclic and their pharmaceutically acceptable, nontoxic acid addition salts and where R or $R_9$ or both are hydroxy, their pharmaceutically acceptable, nontoxic basic salts, possess antihypertensive activity.

23 Claims, No Drawings

N-SUBSTITUTED-AMIDO-AMINO ACIDS

This application is a continuation-in-part of our prior copending application Ser. No. 249,053, filed Mar. 30, 1981, now abandoned.

This invention relates to new chemical compounds having valuable pharmaceutical activity. It particularly relates to compounds possessing antihypertensive and angiotensin converting enzyme inhibitory activity and having the structure

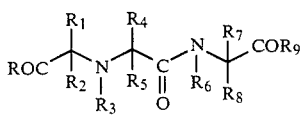

wherein
- R and $R_9$ are independently hydroxy, lower alkoxy, lower alkenoxy, di(lower alkyl)amino-lower alkoxy, hydroxy-lower alkoxy, acylamino-lower alkoxy, acyloxy-lower alkoxy, aryloxy, aryloxyl-lower alkoxy, amino, lower alkylamino, di-lower alkylamino, hydroxyamino, or aryl-lower alkylamino,
- $R_1$, $R_2$, $R_3$, $R_4$, $R_5$, $R_7$ and $R_8$ are independently hydrogen, alkyl having from 1 to 20 carbon atoms, alkenyl having from 2 to 20 carbon atoms, alkynyl having from 2 to 20 carbon atoms, aryl-lower alkyl having from 7 to 12 carbon atoms, or heterocyclic-lower alkyl having from 6 to 12 carbon atoms,
- $R_6$ is heterocyclic,
- $R_2$ and $R_3$ taken together with the carbon and nitrogen to which they are respectively attached and $R_3$ and $R_5$ taken together with the nitrogen and carbon to which they are respectively attached may form an N-heterocycle containing from 3 to 5 carbon atoms or 2 to 4 carbon atoms and a sulfur atom, and
- their pharmaceutically acceptable, nontoxic acid addition salts, and when R or $R_9$ or both are hydroxy, their pharmaceutically acceptable nontoxic basic salts.

The alkyl groups per se or when present as substituents are preferably lower alkyl containing from 1 to 6 carbon atoms and may be straight chain or branched. These groups include methyl, ethyl, propyl, iso-propyl, butyl, isobutyl, amyl, hexyl and the like.

The alkenyl and alkynyl groups per se or when present as substituents preferably contain from 2 to 6 carbon atoms and may be straight chain or branched. These groups include vinyl, propenyl, allyl, isopropenyl, ethynyl and the like.

The alkyl, alkenyl, and alkynyl groups may carry substituents such as hydroxy, lower alkoxy, thio, lower alkylmercapto, amino, lower alkylamino, di(lower alkyl)amino, halogen, and nitro.

The aralkyl and heterocyclic-alkyl groups include benzyl, phenethyl, naphthylmethyl, indolylethyl, indanylmethyl, indanylethyl, pyridylmethyl, indolylmethyl, pyridylethyl, and the like.

By "heterocyclic groups" is meant saturated, partially saturated, and aromatic ring systems containing one or more atoms other than carbon, as well as heterocyclic-lower alkyl groups. These heterocyclic groups include pyrrole, pyrroline, pyrrolidine, pyridine, dihydropyridine, piperidine, morpholine, thiomorpholine, imidazole, imidazoline, imidazolidine, furan, furfuryl, thiophene, benzimidazole, thiazole, thiazoline, thiazolidine, indole, indoline, quinoline, isoquinoline, tetrahydroquinoline, tetrahydroisoquinoline, and the like.

The heterocyclic groups may carry one or more substituents such as lower alkyl, lower alkenyl, lower alkynyl, hydroxy, lower alkoxy, amino, lower alkylamino, di(lower alkyl)amino, thiol, lower alkylmercapto, hydroxy-lower alkyl, amino-lower alkyl, thio-lower alkyl, nitro, halogen, sulfonamide, trifluoromethyl, methylenedioxy, ureido, or guanidino.

The acyl groups are preferably lower alkanoyl containing from 1 to 6 carbon atoms and benzoyl.

The halogen group may be fluorine, chlorine, bromine and iodine.

Suitable acid addition salts may be formed from inorganic acids such as hydrochloric, sulfuric and phosphoric, and organic acids such as acetic, lactic, citric, malic, maleic, fumaric, succinic, benzoic, hydroxybenzoic, aminobenzoic, nicotinic and the like.

Suitable basic salts may include the salts of alkali and alkali earth metals such as sodium, lithium, potassium, magnesium and calcium, as well as iron and salts of ammonia, amines, and quaternaries.

The compounds of the present invention may contain one or more asymmetric carbon atoms each of which may exist in the R or S form. All of these forms and mixtures thereof are contemplated within the scope of the present invention, and the (S), (S,S), and (S,S,S) forms as the case may be are preferred.

The compounds of the present invention are prepared by the reaction of a compound of the formula $$R_6 - NH_2$$

with a compound of the formula

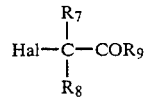

to give a compound of the formula

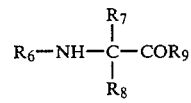

which is then reacted with an ester of the formula

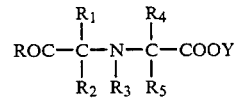

to give the desired compound.

In the above sequence of reactions, R–$R_9$ are the same as described above, Hal is halogen and Y is lower alkyl. It will be recognized by those of ordinary skill in this art that the reaction is advantageously preceded by converting the —OY goup to —OH and then to —Cl; and by converting the $R_9$ and $R_3$ groups to suitable protecting groups such as a lower alkyl ester and 2,2,2-trichloroethoxycarbonyl, respectively, which are subsequently removed as shown in the examples.

Preferably, R and $R_9$ are hydrogen or lower alkyl, $R_2$, $R_5$, $R_7$ and $R_8$ are hydrogen, $R_1$ is phenyl-lower alkyl, $R_3$ is hydrogen, $R_4$ is lower alkyl or amino-lower alkyl, and $R_6$ is indole, thienyl, morpholine, pyrrole, or pyridylmethylene.

The compounds of this invention form acid salts with various inorganic and organic acids which are also within the scope of the invention. The pharmaceutically-acceptable acid addition salts of the compounds of the present invention may be prepared by conventional reactions by reacting the free amino acid or amino ester with an appropriate acid providing the desired anion, either in a solvent or medium in which the salt is insoluble, or in water and removing the water by freeze-drying. The salts of strong acids are preferred. As exemplary, but not limiting, of pharmaceutically-acceptable acid salts are the salts of hydrochloric, hydrobromic, sulfuric, nitric, acetic, fumaric, malic, maleic and citric acids.

The action of the enzyme renin or angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds within the scope of this invention which intervene in the renin -to- angiotensin I -to- angiotensin II sequence inhibit angiotensin I converting enzyme and therefore are useful in reducing or relieving hypertension.

Furthermore, the compounds within the scope of the present invention which possess diuretic activity promote relief from hypertension by promoting diuresis, and consequently have utility in treating congestive heart failure. Compounds within the scope of this invention can also simultaneously possess ACE inhibitory and diuretic activity, which is particularly unexpected in view of the fact that such simultaneous activity cannot be predicted from prior art compounds. Thus by the administration of a composition conaining one or a combination of compounds of formula (1 ) or pharmaceutically-acceptable salts thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day, is appropriate to reduce blood pressure. The substance is preferably administered orally, but a parenteral route such as subcutaneously, intramuscularly, intravenously or intraperitonealy can also be employed.

The compounds of the invention can be utilized to achieve the reduction of blood pressure by formulating one or more of them in compositions such as tablets, capsules or elixirs for oral administration or in sterile solutions or suspensions for parenteral administration. About 10 to 500 mg of a compound or mixture of compounds of formula (1) or physiologically acceptable salt(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; and a disintegrating agent such as corn starch, potato starch, alginic acid and the like; a lubicant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservatives, antioxidants and the like can be incorporated as required.

The invention will be more fully illustrated from the examples which follow. These examples are given by way of illustration and are not to be considered as limiting.

EXAMPLE 1

A. t-Butyl N-[2-(3-Indolyethyl)]-Glycinate

Tryptamine hydrochloride (100 g, 624 mmols) was added to a mixture of acetonitrile(1 l) and concentrated ammonium hydroxide (48.8 ml). Tert-butylbromoacetate (101 g, 518 mmols) in acetonitrile was added dropwise over one hour. The reaction was allowed to stir overnight at room temperature. The solvent was evaporated and the residue was portioned between ethyl acetate and aqueous ammonium hydroxide. The layers were separated and the organic layer was washed with water and brine, dried over magnesium sulfate, filtered and evaporated. The crude product was crystallized from n-hexane/ether to give tan crystals (118 g, 83%); m.p. 88°–90° C.

B. t-Butyl N-(1-(S)-Carbethoxyethyl)-L-Alanyl-N-[2-(3-Indolylethyl)]-Glycinate N-(1-(S)-Carbethoxyethyl)-L-alanine (3.7 g, 0.02 mol) and 1,1'-carbonyldiimidazole (3.6 g, 0.022 mol) were added to dry tetrahydrofuran (30 ml). The resulting mixture was refluxed under nitrogen for thirty minutes. To the resulting solution was added t-butyl N-[2-(3-Indolylethyl)]-glycinate (5.5 g, 0.02 mol) in tetrahydrofuran (15 ml). The resulting mixture was refluxed for two and a half hours. The solvent was evaporated and the residue was dissolved in chloroform. The chloroform was washed twice with water, dried over magnesium sulfate, filtered, and evaporated. The crude product was chromatographed on silica-gel (CHCl$_3$) to give the pure product (8 g, 83%) as a light auburn oil. The product was characterized as its hydrochloride salt; m.p. 140° C.

EXAMPLE 2

A. Benzyl 2-Bromopropionate

2-Bromopropionic acid (750 g, 4.90 moles) and benzyl alcohol (600 g, 3.55 moles) were dissolved in methylene chloride (1500 ml). To the resulting solution was added concentrated sulfuric acid (10 ml). The resulting solution was heated to a gentle reflux for two days, water separating during this time. Water (500 ml) was added and the layers were separated. The methylene chloride was washed with saturated sodium bicarbonate and the layers were separated. The organic layer was washed with water, dried over magnesium sulfate, filtered and evaporated to give a colorless oil which was vacuum distilled to give the pure product as a colorless oil (742 g, 86%).

B. Benzyl N-(1-(S)-Ethoxycarbonyl-3-Methylbutyl)-L-Alanyl-N-[2-(3-Indolylethyl)]-Glycinate N-(1-(S)-Ethoxycarbonyl-3-methylbutyl)-L-alanine (2.31 g, 0.01 mol) and 1,1'-carbonyldiimidazole (2.3 g, 0.0142 mol) were added to dry tetrahydrofuran (40 ml). The resulting mixture was refluxed for fifteen minutes. To the resulting solution was added portionwise benzyl N-(2-indolylethyl)-glycinate (3.08 g, 0.01 mole) dissolved in THF (15 ml). The resulting solution was refluxed for two and a half hours. The solvent was evaporated and the residue was dissolved in ether. The ether was washed three times with water. The ether was dried over magnesium sulfate, filtered, and evaporated to give the crude product. The crude product was chromatographed on silica-gel (ether) to give the pure product (3.8 g, 72%) as a light-colored oil which was a mixture of diastereomers.

EXAMPLE 3

A. t-Butyl N-Carbobenzyloxy-(L-Valyl)-N-[2-(3-Indolylethyl)]-Glycinate t-Butyl N-[2-indolylethyl)-glycinate (12.0 g, 43.8 mmols) was dissolved in methylene chloride (400 ml) and the solution was cooled in an ice bath. Dicyclohexylcarbobiimide (8.2 g, 39.8 mmols) in a small amount of methylene chloride was added. N-carbobenzyloxy-L-valine (10 g, 39.8 mmols) in a small amount of methylene chloride was added dropwise. The reaction was stirred with external cooling for 15 minutes and then at room temperature overnight. Precipitated dicyclohexylurea was filtered and washed with a small amount of methylene chloride. The filtrate was evaporated and ether was added to the residue to precipitate more dicyclohexylurea. The dicyclohexylurea was filtered and the filtrate was evaporated to afford the crude product as a tan gum. The crude product was purified by HPLC using ethyl acetate/methylene chloride (10:90) as eluent to give the pure product as a light tan powder (23.8 g, 91.2%).

B. N-Carbobenzyloxy-(L-Valyl)-N-[2-(3-Indolylethyl)]-Glycine t-Butyl N-carbobenzyloxy (L:valyl)-N-[2-(3-indolylethyl)]glycinate (22.5 g, 44.3 mmols) was dissolved in anisole (47.9 g, 443.2 mmols) and then trifluoroacetic acid (101.1 g, 886.5 mmols) was added. The resulting solution was stirred for three hours at room temperature. Trifluoroacetic acid was removed at 30° C. under vacuum. The dark brown oil was dissolved in ether and the organic extract was washed twice with water and dried over magnesium sulfate. The ether was filtered and evaporated to afford the crude product as a dark oil. The crude product was purified by HPLC eluting with acetic acid/ethyl acetate/n-hexane (2:39:59) to afford the pure product as a pale yellow powder (11.1 g).

EXAMPLE 4

Benzyl N-(1-(S)-Ethoxycarbonyl-2-Phenylethyl)-L-Alanyl-N-[2(3-Indolylethyl)1-Glycinate

[N-(Ethyl 2-phenyl-1-(s)-propionate]-L-alanine (2.65 g, 10.0 mmols) and 1,1'-carbonyldiimidazole (2.0 g, 0.0123 mols) were added to dry tetrahydrofuran (40 ml). The resulting mixture was refluxed for fifteen minutes under nitrogen. To the resulting solution was added portionwise benzyl N-[2(3-Indolylethyl)]glycinate (3.5 g, 11.4 mmols) in a small amount of THF (20 ml). The resulting solution as refluxed for three hours. The solvent was evaporated and the residue was disolved in ether. The ether was washed twice with water, dried over magnesium sulfate, filtered and evaporated to afford an auburn oil. The crude product was chromatographed on silica-gel to afford the pure product as a yellow oil (4.5 g, 81%) which was a mixture of diastereomers.

EXAMPLE 5

A. Ethyl N-Carbobenzyloxy (L-Phenylalanyl-N-[2(3-Indolylethyl)]Glycinate

Ethyl N-[2-(3-indolylethyl)]-glycinate (17.3 g, 0.0703 mol) was dissolved in methylene chloride (400 ml) and the resulting solution was cooled in an ice bath. Dicyclohexylcarbodiimide (16.0 g, 0.078 mol) in a small amount of methylene chloride (25 ml) was added portionwise. N-carbobenzyloxy-L-phenylalanine (21.04 g, 0.0703 mol) was added portionwise. The reaction was stirred with external cooling for fifteen minutes and then for two and a half hours at room temperature. Precipitated dicyclohexylurea was filtered and washed with ether. The filtrate was evporated. The residue was dissolved in ether and washed with 10% HCl, saturated NaHCO₃, water and dried over magnesium sulfate. Filtration and evaporation of the solvent gave a tan viscous oil (33.7 g, 95%).

B. L-Phenylalanyl-N-[2(3-indolylethyl)]-Glycine

N-Carbobenzyloxy-L-phenylalanyl-N-[2-(3-indolylethyl)]glycine (1.3 g, 0.0026 mol) was added to a saturated solution of anhydrous HBr in glacial acetic acid (20 ml) which had been chilled in an ice bath. The resulting solution as stirred for fifteen minutes with external cooling and then for forty-five minutes at room temperature. Most of the acetic acid was evaporated and ether was added to the residue to precipitate the hydrobromide of the product. The hydrobromide was filtered and washed with ether to afford tan crystals (0.85 g, 70.8%); m.p. 140°.

EXAMPLE 6

A. Ethyl N-carbobenzyloxy-L-alanyl-N-(3-thienyl)glycinate

A methylene chloride solution of N-carbobenzyloxy-L-alanine and ethyl (3-thienyl) glycinate was treated with N,N-dicyclobhexylcarbodiimide as in example 5A. The product was applied to silica-gel to afford ethyl N-carbobenzyloxy-L-alanyl-N-(3-thienyl) glycinate.

N-Carbobenzyloxy-L-alanyl-N-(3-thienyl) glycine

An ethanolic solution of ethyl N-carbobenzyloxy-L-alanyl-N-(3-thienyl) glycinate was treated with two equivalents of potassium hydroxide to yield N-carbobenzyloxy-L-alanyl-N-(3-thienyl)glycine.

C. L-alanyl-N-(3-thienyl)glycine

In a manner described in example 5B, N-carbobenzyloxy-L-alanyl-N-(3-thienyl)glycine was treated with anhydrous hydrogen bromide in acetic acid to yield the hydrobromide salt of L-alanyl-N-(3-thienyl)glycine.

EXAMPLE 7

N-(1-Carboxy-3-phenylpropyl)-L-alanyl-N-(3-thienyl)glycine

2-Oxo-4-phenylbutyric acid and L-alanyl-N-(3-thienyl)glycine are condensed in the presence of sodium cyanoborohydride to yield N-(1-carboxy-3-phenylpropyl)-L-alanyl-N-(3-thienyl)glycine.

EXAMPLE 8

A. N-Carbobenzyloxy-L-isoleucyl-N-(3-pyridyl) glycinine

An ethanolic solution of ethyl N-carbobenzyloxy-L-isoleucyl-N-(3-pyridyl) glycinate was treated with potassium hydroxide to yield N-carbobenzyloxy-L-isoleucyl-N-(3-pyridyl)glycine.

B. Ethyl N-Carbobenzyloxy-L-isoleucyl-N-(3-pyridyl)glycinate

A methylene chloride solution of N-carbobenzyloxy-L-isoleucine and ethyl N-(3-pyridyl)-glycinate was treated with N,N-dicyclohexylcarbodiimide as in example 5A. Purification of the product was accomplished by chromatography on silica-gel.

C. L-Isoleucyl-N-(3-pyridyl)glycinate

In a manner described in example 5B, N-carbobenzyloxy-L-isoleucyl-N-(3-pyridyl)-glycine was treated with anhydrous hydrogen bromide in acetic acid to yield L-isoleucyl-N-(3-pyridyl) glycine hydrobromide.

EXAMPLE 9

N-[1-(S)-Ethoxycarbonyl-3-methylbutyl]-L-isoleucyl-N-(3-pyridyl)glycine

Ethyl 4-methyl-2-oxopentanoate and L-isoleucyl-N-(3-pyridyl)-glycine were condensed in the presence of sodium cyanoborohydride to yield N-[1-(S)-ethoxycarbonyl-3-methylbutyl]-L-isoleucyl-N-(3-pyridyl) glycine.

EXAMPLE 10

A. N-Carbobenzyloxy-L-leucyl-N-(2-ethylmorpholine)glycine

An ethanolic solution of ethyl N-carbobenzyloxy-L-leucyl-N-(2-ethylmorpholine) glycinate was treated with potassium hydroxide to yield N-carbobenzyloxy-L-leucyl-N-(2-ethylmorpholine)glycine.

B. Ethyl N-Carbobenzyloxy-L-leucyl-N-(2-ethylmorpholine)glycine

A methylene chloride solution of N-carbobenzyloxy-L-leucine and ethyl N-(2-ethylmorpholine) glycinate was treated with N,N-dicyclohexylcarbodiimide as in Example 5A. The product was purified by chromatography (silica-gel) to yield ethyl N-carbobenzyloxy-L-leucyl-N-(2-ethylmorpholine)glycinate.

EXAMPLE 11

Benzyl N-(1-(S)-ethoxycarbonyl-2-phenylethyl)alanyl-N-(2-benzothiazole)glycinate Benzyl N-[1-(S)-ethoxycarbonyl-2-phenylethyl]alanine and 1,1-carbonyldiimidazole were added to dry tetrahydrofuran. The resulting mixture was refluxed for fifteen minutes. To the resulting solution was added portionwise benzyl N-(2-benzothiozole)glycinate. The resulting mixture was refluxed for three hours. The product was purified in a manner as described in example 1B.

EXAMPLE 12

A. Benzyl N-[1-(S)-Ethoxycarbonylethyl]alanyl-N-(2-pyrimidyl)-glycinate

N-[1-(S)-Ethoxycarbonylethyl]alanine and 1,1'-Carbonyldiimidazole were added to dry tetrahydrofuran. The resulting mixture was refluxed for fifteen minutes. To the resulting solution was added benzyl N-(2-pyrimidyl)glycinate. The resulting mixture was refluxed for three hours. The product was purified by HPLC chromatography to yield benzyl N-[1-(S)ethoxycarbonylethyl]alanyl-N-(2-pyrimidyl)glycinate.

B. N-[1-(S)-Ethoxycarbonylethyl]alanyl-N-(2-pyrimidyl)glycine

Benzyl [N-1-(S)-ethoxycarbonylethyl]alanyl-N-(2-pyrimidyl) glycinate was dissolved in ethanol and 10% Pd/c was added under nitrogen. The reaction mixture was hydrogenated and purified to yield N-[1-(S)-ethoxycarbonylethyl]alanyl-N-(2-pyrimidyl)glycine.

EXAMPLE 13

N-(morpholin-1-yl)-N-[N-[(1S)-1-ethoxycarbonyl-3-phenylpropyl]-L-alanyl]glycine dihydrochloride To a mixture of N-[(1S)-ethoxycarbonyl-3-phenylpropyl]-L-alanine (10 g) and sulfuric acid (10 ml) in 100 ml of dioxane was added 150 ml of isobutylene, and the resulting reaction mixture was shaken in a pressure bottle overnight. The reaction mixture was neutralized with 50% NaOH, taken up in 200 ml of ethyl acetate, and washed with water. The organic solution as dried and evaporated to dryness to give 10 g of an oily product (13-A), N-[(1S)-Ethoxycarbonyl-3-phenylpropyl]-L-alanine t-butyl ester.

A mixture containing 2.52 g (7.51 mmol) of compound (13-A), 1.10 ml (7.99 mmol) of 2,2,2-trichloroethyl chloroformate, and 1.0 ml (12.4 mmol) of pyridine in 25 ml of dry tetrahydrofuran was refluxed under a nitrogen atmosphere for 3 hours. The reaction mixture was filtered, taken up in 200 ml of ether, and washed four times with 1 N hydrochloric acid and once with brine. The organic phase as dried over MgSO$_4$, filtered, and concentrated in vacuo to yield 3.79 g (99%) of compound (13-B), N-[(1S)-1-ethoxycarbonyl-3-phenylpropyl]-N-(2,2,2-trichloroethoxycarbonyl)-L-alanine t-butyl ester.

A mixture containing 1.98 g (3.88 mmol) of compound (13-B) in 25 ml of 4 N HCl in dioxane at room temperature and under a nitrogen atmosphere was stirred for 8 hours. The mixture was then concetrated in vacuo to provide 1.77 g (100%) of compound (13-C), N-[(1S)-1-ethoxycarbonyl-3-phenylpropyl]-N-(2,2,2-trichloroethoxycarbonyl)-L-alanine.

To a mixture containing 908 mg (2.00 mmol) of compound (13-C) and 0.40 ml (4.6 mmol) of oxalyl chloride in 10 ml of dry methylene chloride at room temperature and under a nitrogen atmosphere was added 10 L (0.13 mmol) of N,N-dimethylformamide. After two hours the mixture was carefully concentrated in vacuo (T<30° C.) to give 900 ml of compound (13-D), N-[(1S)-ethoxycarbonyl-3-phenylpropyl]-N-(2,2,2-trichloroethoxycarbonyl)-L-alanyl acid chloride.

A mixture of N-aminomorpholine (4 g), t-butyl bromoacetate (7.6 g) and sodium carbonate (2.1 g) in 20 ml of DMF was stirred at room temperature overnight. After concentration in vacuo, the residue was taken up in ethyl acetate. The organic solution was washed with water, dried, filtered and concentrated in vacuo to give 2.5 g of crude N-(morpholin-1-yl)glycine t-butyl ester (compound 13-E). This crude compound was used without further purification. To a solution of 5 g of product (13-D) in 10 ml of methylene chloride was added a solution of 2.5 g of compound (13-E) and 5 ml of pyridine in 5 ml of methylene chloride over a period of 10 minutes. After 16 hours the reaction mixture was washed successively with 1N hydrochloric acid, saturated aqueous sodium bicarbonate, and once with brine. The organic solution was dried, filtered, concentrated in vacuo, and purified by dry colunn chromatography to give 3.5 g of oily product (13-F), N-(morpholin-1-yl)-N-[N-[(1S)-1-ethoxycarbonyl-3-phenylpropyl]-N-(2,2,2-trichlororethoxycarbonyl)-L-alanyl]glycine t-butyl ester.

To a solution of 0.6 g of product (13-F) in 10 ml of glacial acetic acid was added 2 g of zinc dust. After three hours the mixture was filtered through celite and concentrated in vacuo. The residue was taken up in ethyl acetate and washed with water. The organic solution was dried, filtered, concentrated in vacuo, and chromatographed to give 0.4 g of product (13-G), N-(morpholin-1-yl)-N-[N-[(1S)-1-ethoxycarbonyl-3-phenylpropyl]L-alanyl]glycine t-butyl ester.

The dihydrochloric acid salt of the free acid was formed by bubbling dry hydrogen chloride gas into an etheral solution containing 0.5 g of product (13-G) at 0° C. for 2.5 hours. Concentration in vacuo gave 0.4 g of solid product, m.p. 110° C. (decomposes).

EXAMPLE 14

N-[Nα-[(1S)-ethoxycarbonyl-3-phenylpropyl]-L-lysyl]-N-(morpholin-1-yl)glycine dihydrobromide To a miture of Nα-[(1S)-ethoxycarbonyl-3-phenylpropyl]-Nα-(2,2,2-trichloroethoxycarbonyl)-Nε-carbobenzyloxy-L-lysine (3.95 g) (prepared by a procedure analogous to compound (13-C)) and 1.2 ml of oxalyl chloride in 25 ml of methylene chloride was added a few drops of dimethyl formamide in 1 ml of methylene chloride under a nitrogen atmosphere. After stirring the mixture for 2 hours, the solvent was removed and the residue dissolved in 30 ml of methylene chloride. This mixture was added dropwise to a solution of 2 g of (compound 13-E) and 1.8 ml of pyridine in 10 ml of methylene chloride. The resulting mixture was stirred for 18 hours. The reaction mixture was taken up in 200 ml of ether and washed successively in 30 ml portions of saturated aqueous sodium bicarbonate, 1 N HCl, saturated aqueous sodium bicarbonate, and 50% brine. Removal of solvent after drying yielded 5.7 g of crude product which was purified by dry column chromatography (hexanes: ethyl acetate=2:1) to yield 1.5 g of N-[Nα-[(1S)ethoxycarbonyl-3-phenylpropyl]-Nα-(2,2,2-trichloroethoxycarbonyl)-Nεcarbobenzyloxy-L-lysyl]-N-(morpholin-1-yl)glycine t-butyl ster. This product was mixed in 15 ml of glacial acetic acid to which 1.8 g of zinc dust was added, to remove the Nα-protecting group. This mixture was stirred overnight at room temperature. Removal of solvent in vacuo yielded 1.3 g of the crude mixture as a pale yellow oil. The crude mixture was purified by cry column chromatography (ethyl acetate: hexanes=2.1) to provide 450 mg of N-[Nα-[(1S) ethoxycarbonyl-3-phenylpropyl]-Nε-carbobenzyloxy-L-lysyl]-N-(morpholin-1-yl)glycine t-butyl ester. The Nε-protecting group was removed, and the ester was converted to the free acid hydrobromide, by adding 1.5 ml of a 50:50 mixture of HBr in acetic acid to 450 mg of the product from the preceding step, and letting the mixture stand for 1 hour at room temperature. To this mixture anhydrous ether was then added dropwise with swirling. A white precipitate formed which was collected by filtration. The precipitate was washed with ether and dried under vacuum. The product was 350 mg of N-[Nα-[(1S)-ethoxycarbonyl-3-phenylpropyl]-L-lysyl]-N- (morpholin-1-yl)glycine dihydrobromide, m.p. 165° C. (decomposes).

EXAMPLE 15

N-[1-(2-methylindolino)]-N-[N-[(1S)-1-ethoxycarbonyl-3-phenylpropyl]-L-alanyl[glycine dihydrochloride A mixture of 1-amino-2-methylindoline (3.7 g), potassium carbonate (2.8 g) and t-butyl bromoacetate (4 g) in 10 ml of DMF was stirred at room temperature overnight. After removal of DMF in vacuo, the residue was taken up in ethyl acetate. The organic solution was washed with water, dried with magnesium sulfate, filtered, and concentrated. The product was purified by dry column chromatography to give 1.5 g of slightly impure oily product (14-A), N-[1-(2-methylindolino)]glycine t-butyl ester. This was used for the next reaction without further purification.

A solution of 2.25 g of acid chloride product (13-D) in 10 ml of methylene chloride was added dropwise to a 15 ml of methylene chloride solution containing 1.5 g of product (14-A) and 0.4 g of pyridine over a period of 10 minutes. After 20 hours the reaction mixture was washed successively with 1 N hydrochloric acid, saturated aqueous sodium bicarbonate, and brine solution. The organic solution was dried, filtered, concentrated and purified by dry column chromatography to give 2 g of product (14-B), N-[1-(2-methylindolino)]-N-[N-[(1S)-1-ethoxy-carbonyl-3-phenylpropyl]-N-(2,2,2-trichloro-ethyoxycabonyl)-L-alanyl]glycine t-butyl ester.

To a solution of 2 g of the product (14-B) in 10 ml of acetic acid was added 4 g of zinc dust. After 2 hours the reaction mixture was filtered through celite and concentrated in vacuo. The residue was purified by dry column chromatography to give 0.8 g of oily product (14-C), N-[1-(2-methylindolino)]-N-[N-[(1S)-1-ethoxycarbonyl-3-phenylpropyl]-L-alanyl]glycine t-butyl ester:

The dihydrochloric acid salt of the free acid was prepared by bubbling dry hydrogen chloride gas into an etheral solution containing 0.8 g of product (14-C) at 0°

C. for 2 hours. Concentration in vacuo gave 0.4 g of solid product, m.p. 60°–64° C.

EXAMPLE 16

N-[N-[(1S)-Ethoxycarbonyl-3-phenylpropyl]-L-alanyl]-N-(pyrroll-yl)glycine hydrochloride Using the procedure employed in Example 14, compound (13-C) (5 g) was reacted with 0.96 ml of oxalyl chloride to form the acid chloride, which was reacted with N-(pyrrol-1-yl) glycine t-butyl ester which had previously been made by the procedure employed to make compound (13-E) using N-aminopyrrole instead of N-aminomorpholine. The reaction product (4 g) was de-N-protected in 20 ml of glacial acetic acid with 3.1 g of zinc dust, and this mixture was stirred at room temperature overnight under a nitrogen atmosphere. After removal of solvent and washing, which yielded 2.2 g of a reddish-brown oil, this product was purified by dry column chromatography (25% ethyl acetate in hexanes) to yield 0.7 g of a pale yellow oil, N-[N-[(1S)-ethoxycarbonyl-3-phenylpropyl]-L-alanyl]-N-(pyrrol-1-yl)glycine t-butyl ester. This product was dissolved in 25 ml of ether in an ice bath, HCl gas was bubbled through the solution for 3 hours, and the solution was then allowed to stand for 1.5 hours more. Removal of solvent gave 390 mg of a slightly orange powder, N-[N-[(1S)-ethoxycarbonyl-3-phenylpropyl]-L-alanyl]-N-(pyrrol-1-yl)glycine hydrochloride, m.p. 110°–118° C. (decomposes).

EXAMPLE 17

N-(4-Methylpiperazin-1-yl)-N-[N-[(1S)-1-ethoxycarbonyl-3-phenylpropyl]-L-alanyl]glycine t-butyl ester and the free acid are made by the same procedure employed for Example 13, substituting N-amino-N'-methylpiperazine for N-aminomorpholine.

EXAMPLE 18

N-(Tetrahydro-1,4-thiazin-4-yl)-N-[N-[(1S)-1-ethoxycarbonyl-3-phenylpropyl]-L-alanyl]glycine t-butyl ester and the free acid are made by the same procedure employed for Example 13, substituting N-amino-tetrahydro-1,4-thiazine for N-aminomorpholine.

EXAMPLE 19

N-(Thiazolidin-3-yl)-N-[N-[(1S)-1-ethoxycarbonyl-3-phenylpropyl]-L-alanyl]glycine t-butyl ester and the free acid are made by the same procedure employed for Example 13, substituting N-amino-thiazolidine for N-aminomorpholine.

EXAMPLE 20

N-(Piperidin-1-yl)-N-[N-[(1S)-1-ethoxycarbonyl-3-phenylpropyl]-L-alanyl]glycine t-butyl ester and the free acid are made by the same procedure employed for Example 13, substituting N-amino-piperidine for N-aminomorpholine.

EXAMPLE 21

N-(Pyrrolidin-1-yl)-N-[N-[(1S)-1-ethoxycarbonyl-3-phenylpropyl]-L-alanyl]glycine t-butyl ester and the free acid are made by the same procedure employed for Example 13, substituting N-amino-pyrrolidine for N-aminomorpholine.

EXAMPLE 22

N-(2,3-Dihydroindol-1-yl)-N-[N-[(1S)-1-ethoxycarbonyl-3-phenylpropyl]-L-alanyl]glycine t-butyl ester and the free acid are made by the same procedure employed for Example 13, substituting N-amino-2,3-dihydroindole for N-aminomorpholine.

EXAMPLE 23

N-(1,2,3,4-Tetrahydroisoquinolin-2-yl)-N-[N-[(1S)-1-ethoxycarbonyl-3-phenylpropyl]-L-alanyl]glycine t-butyl ester and the free acid are made by the same procedure employed for Example 13, substituting N-amino-1,2,3,4-tetrahydroisoquinoline for N-aminomorpholine.

EXAMPLE 24

N-(Imidazol-1-yl)-N-[N-[(1S)-1-ethoxycarbonyl-3-phenylpropyl]-L-alanyl]glycine t-butyl ester and the free acid are made by the same procedure employed for Example 13, substituting N-amino-imidazole for N-aminomorpholine.

EXAMPLE 25

N-[N-[(1S)-Ethoxycarbonyl-3-phenylpropyl]-S-alanyl]-N-(3-pyridylmethylene)glycine dihydrochloride Acetonitrile (300 ml) was added to 3-aminomethylpyridine (21.6 g, 0.2 mole) followed by the addition of water (20 ml) and concentrated ammonium hydroxide (20 ml). To the resulting stirring solution tert-butyl bromoacetate (30 g, 0.2 mole) in acetonitrile (75 ml) was added dropwise to room temperature. The acetonitrile was evaporated on a rotary evaporator and then water was added to the residue and the product was extracted several times into methylene chloride. The combined methylene chloride extract was washed several times with water, dried over magnesium sulfate, filtered and concentrated to afford the crude product as a tan oil. The crude product was purified by silica-gel chromatography using methylene chloride as eluent. The desired product fractions were combined and concentrated to afford the desired product as an orange oil. The hydrochloride was prepared using anhydrous hydrogen chloride in ether to afford tert-butyl N-(3-pyridylmethylene) glycinate hydrochloride as a colorless powder (30.5 g, 59%); m.p. 142° C.; mass spectra (CI): 223 (M+1, 100%). (Analysis: calcd. for $C_{12}H_{18}N_2O_2 \cdot HCl$: C, 55.70; H, 7.40; N, 10.83; found: C, 55.11; H, 7.19; N, 10.50.)

tert-Butyl N-[N-[(1S)-ethoxycarbonyl-3-phenylpropyl]-(S)-alanyl]-N-(3-pyridylmethylene)glycinate hydrochloride To N-[N-[(1S)-ethoxycarbonyl-3-phenylpropyl]-(S)-alanyl]-N-carboxyanhydride (1.5 g, 4.92 mmol) in methylene chloride (30 ml) was added tert-butyl N-(3-methylpyridine) glycinate (1.4 g, 6.3 mmole). The resulting solution was stirred overnight at room temperature. The solvent was evaporated and the residue was chromatographed over silica-gel using methylene chloride as eluent. The desired product fractions were combined and concentrated to give pure tert-butyl N-[N-[1-(S)ethoxycarbonyl-3-phenylpropyl]-(S)-alanyl]-N-(3-pyridylmethylene) glycinate hydrochloride as a light colored oil (1.3 g, 54%). The hydrochloride of the product was prepared using anhydrous ether saturated with anhydrous hydrogen chloride to give a colorless solid which was filtered and washed with cold anhydrous ether: m.p. 76° C.; mass spectra (CI): 484.9 M+1, 100%); $[a]_{365}^{CHCl_3} = +50.99°$; $[a]_{546}^{CHCl_3} = +61.36°$; $[a]_{436}^{CHCl_3} = +109.64°$; $[a]_{365}^{CHCl_3} = +178.26°$. (Analysis: calcd. for $C_{27}H_{37}N_2O_5.2HCl$: C, 54.68; H, 6.29; N, 7.09; found: C, 54.59; H, 6.46; N, 7.32.).

N-[N-[(1S)-Ethoxycarbonyl-3-phenylpropyl]-(S)-alanyl]-N-(3-pyridylmethylene)glycine dihydrochloride To tert-butyl N-[N-[(1S)-ethoxycarbonyl-3-phenylpropyl]-(S)-alanyl]-N-(3-pyridylmethylene)glycinate (0.6 g, 1.24 mmoles) was added p-dioxane (30 ml) which had been saturated with anhydrous hydrogen chloride. The resulting solution was stirred for two and half hours at room temperature and then the solvent was evaporated to afford the desired product as a colorless powder (0.495 g, 86%); m.p. 77°; $[a]_D^{EtOH} = +14.04°$; mass spectra (CI): 410 (m+1-H$_2$O, 100%). (Analysis: calcd. for $C_{23}H_{29}N_3O_5.2HCl.2H_2O$: C, 51.49; H, 6.58; N, 7.83; found: C, 51.28; H, 6.86; N, 7.32.)

EXAMPLE 26

N-[N-[(1S)-Ethoxycarbonyl-3-phenylpropyl]-S-alanyl]-N-(2-pyridylmethylene)glycine t-butyl ester and the free acid are prepared by the same procedure employed in Example 25, substituting 2-aminomethylpyridine for 3-aminomethylpyridine.

EXAMPLE 27

N-[N-[(1S)-Ethoxycarbonyl-3-phenylpropyl]-S-alanyl]-N-(4-pyridylmethylene)glycine t-butyl ester and the free acid are prepared by the same procedure employed in Example 25, substituting 4-aminomethylpyridine for 3-aminomethylpyridine.

EXAMPLE 28

N-[N-[(1S)-Ethoxycarbonyl-3-phenylpropyl]-S-alanyl]-N-(furfuryl)glycine t-butyl ester and the free acid are prepared by the same procedure employed in Example 25, substituting 2-aminomethylfuran for 3-aminomethylpyridine.

EXAMPLE 29

N-[N-[(1S)-Ethoxycarbonyl-3-phenylpropyl]-S-alanyl]-N-(2-thienylmethylene)glycine t-butyl ester and the free acid are prepared by the same procedure employed in Example 25, substituting 2-aminomethylthiophene for 3-aminomethylpyridine.

EXAMPLES 30–34

The compounds having the structures shown in the following Table as Examples 30–34 are made by the procedure of Example 25, starting from NH$_2$-X instead of 3-aminomethylpyridine.

TABLE

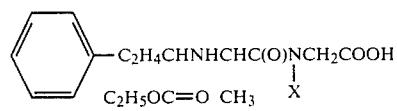

| Example | X |
|---|---|
| 13 | —N⟨O⟩ (morpholino) |
| 15 | N-methylindoline group |
| 25 | —CH$_2$-(3-pyridyl) |
| 29 | —CH$_2$-(2-thienyl) |
| 30 | fused cyclopentyl-pyridine (isomer) |
| 31 | fused cyclopentyl-pyridine (isomer) |
| 32 | fused cyclopentyl-furan |
| 33 | fused cyclopentyl-thiophene |
| 34 | fused cyclopentylpyrrole (NH) | one species of (fused cyclopentylpyrrole)

By following the procedures in the above examples, the following additional compounds were prepared:

N-[1-(S)-Ethoxycarbonyl-2-phenylethyl]alanyl-N-(furfuryl)glycine

N-[1-(S)-Ethoxycarbonyl-3-methylbutyl]alanyl-N-(3-pyridyl)glycine

N-[1-(S)-Ethoxycarbonyl-3-phenylpropyl]alanyl-N-(tetrahydrofurfuryl)-glycine

N-[1-(S)-Ethoxycarbonyl-2-methylthioethyl]alanyl-N-[1-methyl-3-(2-indolylethyl)]-glycine N-[1-Ethoxycarbonyl-4-methylpentyl]alanyl-N-(2-benzothiazole) alanine N-[1-(S)-Ethoxycarbonyl-3-phenylpropyl]alanyl-N-(2-ethylmorpholine) glycine N-[1-(S)-Ethoxycarbonyl-2-(3-indole)ethyl]alanyl-N-[(2-ethyl) pyrrolidine]glycine N-[1-(S)-Ethoxycarbonylethyl]valyl-N-(5-indolyl)glycine N-(1,3-Dicarboxypropyl)leucyl-N-(1,4-benzodioxan-6-yl)glycine
N-[1-(S)-Ethoxycarbonylethyl]isoleucyl-N-(5-benzofurfuryl)glycine
N-[1-(S)-Carboxyethyl]alanyl-N-(3-thienyl)glycine
N-[1-(S)-Carboxy-3-phenylpropyl]phenylalanyl-N-(3-thiazolyl)glycine
N-[1-(S)-Ethoxycarbonyl-2-phenylethyl]alanyl-N-(2-thienyl)glycine
N-(1,3-Diethoxycarbonylpropyl)-P-chlorophenylalanyl-N'-(2-pyrimidyl)glycine
N-(1-(S)-Carboxy-3-methylbutyl)alanyl-N-(tetrahydrothiophene-1,1-dioxide-3yl)-lysine
N-(1-(S)-Ethoxycarbonyl-3-phenylpropyl)valyl-N-(N-ethylpiperidine-3-yl)-lysine
N-(1-(S)-Carboxy-2-phenylethyl)-phenylalanyl-N'-(4-tetrahydrothiopyranyl)-glycine The compounds of the present invention have demonstrated potent activity (of the order of $I_{50}$ or 1.0 to 50.0 micromols) in inhibiting the angiotensin converting enzyme (ACEI activity) when tested by the method described in Science 196, 441-4 (1977). The compounds of the present invention have also demonstrated an $I_{50}$ of about 1 to 10 mg/kg P.O. in inhibiting infused angiotensin I in rats. As such, these would be very useful in the treatment of hypertension.

We claim:
1. Compounds of the formula

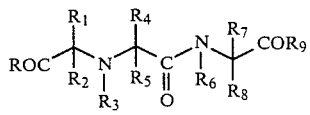

wherein R and $R_9$ are independently hydroxy or lower alkoxy,
$R_1$ and $R_2$ are independently hydrogen, lower alkyl, or aryl-lower alkyl having from 7 to 12 carbon atoms,
$R_3$, $R_4$, $R_5$, $R_7$ and $R_8$ are hydrogen or lower alkyl,
$R_6$ is a heterocyclic group selected from the group consisting of pyrrolyl, pyrrolinyl, pyrrolidinyl, pyridinyl, dihydropyridinyl, piperidinyl, morpholinyl, thiomorpholinyl, imidazolyl, imidazolinyl, imidazolidinyl, furanyl, furfuryl, thienyl, benzimidazolyl, thiazolyl, thiazolinyl, thiazolidinyl, indolyl, quinolinyl, isoquinolinyl, tetrahydroquinolinyl, tetrahydroisoquinolinyl, and indolylethyl,
and wherein
alkyl where present can carry at least one substituent selected from the group consisting of hydroxy, lower alkoxy, thio, lower alkylmercapto, amino, lower alkylamino, di(lower alkyl) amino, halogen, and nitro;
the heterocyclic group can carry at least one substituent selected from the group consisting of lower alkyl, hydroxy, lower alkoxy, halogen and trifluoromethyl; and
their pharmaceutically acceptable, nontoxic acid addition salts and where R or $R_9$ or both are hydroxy, their pharmaceutically acceptable basic salts.

2. Compounds of the formula

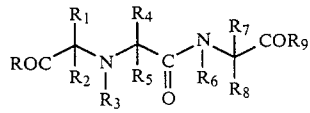

wherein
R and $R_9$ are independently hydroxy, lower alkoxy, lower alkenoxy, di(lower alkyl)amino-lower alkoxy, hydroxy-lower alkoxy, acylamino-lower alkoxy, acyloxy-lower alkoxy, aryloxy, aryloxy-lower alkoxy, amino, lower alkylamino, di-lower alkylamino, hydroxyamino, or aryl-lower alkylamino,
$R_1$, $R_2$, $R_3$, $R_4$, $R_5$, $R_7$ and $R_8$ are independently hydrogen, alkyl having from 1 to 20 carbon atoms, alkenyl having from 2 to 20 carbon atoms, alkynyl having from 2 to 20 carbon atoms, aryl-lower alkyl having from 7 to 12 carbon atoms, or heterocyclic-lower alkyl having from 6 to 12 carbon atoms,
$R_6$ is a heterocyclic group,
$R_2$ and $R_3$ taken together with the carbon and nitrogen to which they are respectively attached and $R_3$ and $R_5$ taken together with the nitrogen and carbon to which they are respectively attached may form an N-heterocycle containing from 3 to 5 carbon atoms or 2 to 4 carbon atoms and a sulfur atom, and wherein
the alkyl, alkenyl, and alkynyl groups may carry substituents selected from the group consisting of hydroxy, lower alkoxy, thio, lower alkylmercapto, amino, lower alkylamino, di(lower alkyl)amino, halogen, and nitro;
the heterocyclic groups are selected from the group consisting of pyrrole, pyrroline, pyrrolidine, pyridine, dihydropyridine, piperidine, morpholine, thiomorpholine, imidazole, imidazoline, imidazolidine, furan, furfuryl, thiophene, benzimidazole, thiazole, thiazoline, thiazolidine, indole, quinoline, isoquinoline, tetrahydroquinoline, tetrahydroisoquinoline, and indolylethyl,
the heterocyclic groups may carry one or more substituents selected from the group consisting of lower alkyl, lower alkenyl, lower alkynyl, hydroxy, lower alkoxy, amino, lower alkylamino, di(lower alkyl)amino, thiol, lower alkylmercapto, hydroxy-lower alkyl, amino-lower alkyl, thio-lower alkyl, nitro, halogen, sulfonamide, trifluoromethyl, methylenedioxy, ureido, and guanidino; and
their pharmaceutically acceptable, nontoxic acid addition salts and where R or $R_9$ or both are hydroxy, their pharmaceutically acceptable basic salts.

3. The compounds and salts according to claim 1 wherein $R_1$ is lower alkyl or phenyl-lower alkyl, and $R_2$, $R_3$, $R_5$, $R_7$ and $R_8$ are hydrogen.

4. The compounds and salts according to claim 3 wherein one or both of R and $R_9$ is hydroxy.

5. The compounds and salts according to claim 3 wherein R is ethoxy.

6. The compounds and salts according to claim 5 wherein $R_4$ is methyl.

7. The compounds and salts according to claim 5 wherein $R_1$ is benzyl or phenethyl and $R_4$ is methyl or omega-amino-n-butyl.

8. The compounds and salts according to claim 7 wherein $R_6$ is indolylethyl.

9. The compounds and salts according to claim 7 wherein $R_1$ is benzyl.

10. The compounds and salts according to claim 7 wherein $R_1$ is phenethyl.

11. A method of reducing the blood pressure in hypertensive animals which comprises the administration of an antihypertensively effective amount of a compound according to claim 1.

12. The compound according to claim 7 which is N-(morpholin-1-yl)-[N-(Nα-[(1S)-ethoxycarbonyl-3-phenylpropyl]-L-lysinyl]glycine, its lower alkyl esters, and pharmaceutically acceptable salts thereof.

13. The compound according to claim 7 which is N-(morpholin-1-yl)-N-[N-[(1S)-ethoxycarbonyl-3-phenylpropyl]-L-alanyl]glycine, its lower alkyl esters, and pharmaceutically acceptable salts thereof.

14. The compound according to claim 7 which is N-(pyrrol-1-yl)-N-[N-[(1S)-ethoxycarbonyl-3-phenylpropyl]-L-alanyl]glycine, its lower alkyl esters, and pharmaceutically acceptable salts thereof.

15. The compound according to claim 7 which is N-(thiazolidin-1-yl)-N-[N-[(1S)-ethoxycarbonyl-3-phenylpropyl]-L-alanyl]glycine, its lower alkyl esters, and pharmaceutically acceptable salts thereof.

16. The compound according to claim 7 which is N-(piperidin-1-yl)-N-[N-[(1S)-ethoxycarbonyl-3-phenylpropyl]-L-alanyl]glycine, its lower alkyl esters, and pharmaceutically acceptable salts thereof.

17. The compound according to claim 7 which is N-(pyrrolidin-1-yl)-N-[N-[(1S)-ethoxycarbonyl-3-phenylpropyl]-L-alanyl]glycine, its lower alkyl esters, and pharmaceutically acceptable salts thereof.

18. The compound according to claim 7 which is N-(1,2,3,4-tetrahydroisoquinolin-2-yl)-N-[N-[(1S)-ethoxycarbonyl-3-phenylpropyl]-L-alanyl]glycine, its lower alkyl esters, and pharmaceutically acceptable salts thereof.

19. The compound according to claim 7 which is N-(imidazol-1-yl)-N-[N-[(1S)-ethoxycarbonyl-3-phenylpropyl]-L-alanyl]glycine, its lower alkyl esters, and pharmaceutically acceptable salts thereof.

20. The compound according to claim 7 which is N-(furfuryl)-N-[N-[(1S)-ethoxycarbonyl-3-phenylpropyl]-L-alanyl]glycine, its lower alkyl esters, and pharmaceutically acceptable salts thereof.

21. The compound according to claim 7 which is N-(2-thienylmethylene)-N-[N-[(1S)-ethoxycarbonyl-3-phenylpropyl]-L-alanyl]glycine, its lower alkyl esters, and pharmaceutically acceptable salts thereof.

22. The compound according to claim 7 which is N-(2-(3-indolylethyl))-N-[N-[(1S)-ethoxycarbonyl-3-phenylpropyl]-L-alanyl]glycine, its lower alkyl esters, and pharmaceutically acceptable salts thereof.

23. A pharmaceutical preparation comprising an antihypertensive effect amount of one or more compounds or salts of claim 1 in association with a pharmaceutically acceptable carrier.

* * * * *